United States Patent [19]

Klemm

[11] Patent Number: Plant 6,500

[45] Date of Patent: Dec. 27, 1988

[54] CARNATION NAMED KLEFITOP

[76] Inventor: Siegfried Klemm, Hanfacker 8, D 7000 Stuttgart 50, Fed. Rep. of Germany

[21] Appl. No.: 938,558

[22] Filed: Dec. 5, 1986

[51] Int. Cl.[4] ..... A01H 5/00

[52] U.S. Cl. ..... Plt./70

[58] Field of Search ..... Plt./70

*Primary Examiner*—Robert E. Bagwill

*Attorney, Agent, or Firm*—Charles W. Rummler

[57] ABSTRACT

A new variety of carnation cultivar distinguished by the venetian pink coloring of its medium sized blooms including some petals having a very few cardinal red stripes extending longitudinally from the serrated petal tips, which are borne on sturdy pedicels carried by long, strong peduncles and by its continuous and profuse production of flowers.

1 Drawing Sheet

BACKGROUND OF THE NEW PLANT

This new carnation cultivar originated at Stuttgart, West Germany, as a sport of an unpatented carnation variety named "Ministar", being grown in my greenhouses for the production of cut flowers, as well as for propagation and sale of plants to commercial growers for spray carnation uses. This sport was discovered by me in my greenhouses at Stuttgart, West Germany in 1980 and was selected for propagation because of its venetian pink coloration. Asexual reproduction of this plant has occurred in West Germany, Italy and Israel. Through successive generations has demonstrated that its distinguishing characteristics hold true from generation to generation and appear to be firmly fixed.

DESCRIPTION OF THE DRAWINGS

My new carnation cultivar is illustrated by the accompanying full color photographic drawing, which shows several flower stems, of the plant, including buds in various stages of formation and of opening, as well as fully opened flowers, the colors shown being as nearly true as can be obtained by conventional professional photographic procedures.

DESCRIPTION OF THE NEW PLANT

The following is a detailed description of my new carnation cultivar based upon observation of plants grown under conventional greenhouse procedures at Stuttgart, West Germany, the color designation being according to The R.H.S. Colour Chart published by The Royal Horticultural Society of London, England.

THE PLANT

Origin: Sport.
Parentage: Ministar (unpatented).
Classification:
- *Botanic.—Dianthus carophyllus.*
- *Commercial.*—Spray carnation.

Form: Bush.
Height: About 100 cm. to about 130 cm.
Growth: Vigorous and upright with good strength.
Branching: Normal.
Foliage:
- *Quantity.*—Moderate.
- *Leaf size.*—Moderate.
- *Leaf shape.*—Oblong.
- *Texture.*—Smooth.

- *Color.*—Upper side — blue-green. Under side — blue-green.

THE BUD

Size: Medium, about 15 mm. in diameter and about 45 mm. long.
Form: Generally ovoid.
Color:
- *When sepals first divide.*—Medium pink.
- *When petals begin to unfurl.*—Medium pink.

Sepals:
- *Condition.*—Upstanding.
- *Number.*—About 5.
- *Color.*—Inside — gray-green. Outside — yellow-green.

Calyx:
- *Shape.*—Cylindrical.
- *Size.*—About 14 mm. broad and about 18 mm. long.
- *Splitting.*—The calyx does not split.
- *Aspect.*—Smooth.
- *Peduncle.*—Rigid and erect.
- *Color.*—Gray-green.

THE FLOWER

Blooming habit: Continuous and profuse.
Size of bloom: Medium.
- *Diameter.*—About 70 mm.
- *Depth.*—About 25 mm. to about 30 mm.

Borne: Singly on strong, upright pedicel.
Shape: High-centered when the bloom opens and this shape does not change.
Petalage:
- *Number of petals.*—About 31.
- *Arrangement.*—Generally imbricated.
- *Shape.*—Fan-shaped.
- *Color.*—Outer and inside petals — R.H.S. 50D-49C with some petals having fine cardinal red stripes extending lengthwise from tips of the petal ruffles. Reverse side — R.H.S. 50D-49C.
- *Texture.*—Soft.
- *Appearance.*—Shiny.

Peduncle: Sturdy and upright.
- *Length.*—About 50 cm.
- *Color.*—Gray-green.

Persistence: The petals hang on and dry and the bloom stays upright.
Fragrance: None.
Lasting quality:

*On plant.*—About 15 days.
*As a cut flower.*—About 12 days.

REPRODUCTIVE ORGANS

Stamens: Anthers and pollen are rarely present.
*Pistils.*—About 3 with a length of about 18 mm.
*Styles.*—Length — about 20 mm. to about 40 mm.
*Fruit.*—Fertile.
*Shape.*—Cylindrical.
*Color.*—Green/Brown at maturity.

I claim:

1. A new and distinct carnation cultivar, substantially as herein shown and described, characterized by its high productivity of venetian pink flowers having cardinal red stripes extending lengthwise on petals from the tips of petal ruffles, said flowers are borne singly on rigid, erect pedicels carried in spray formation on a sturdy and upright peduncle.

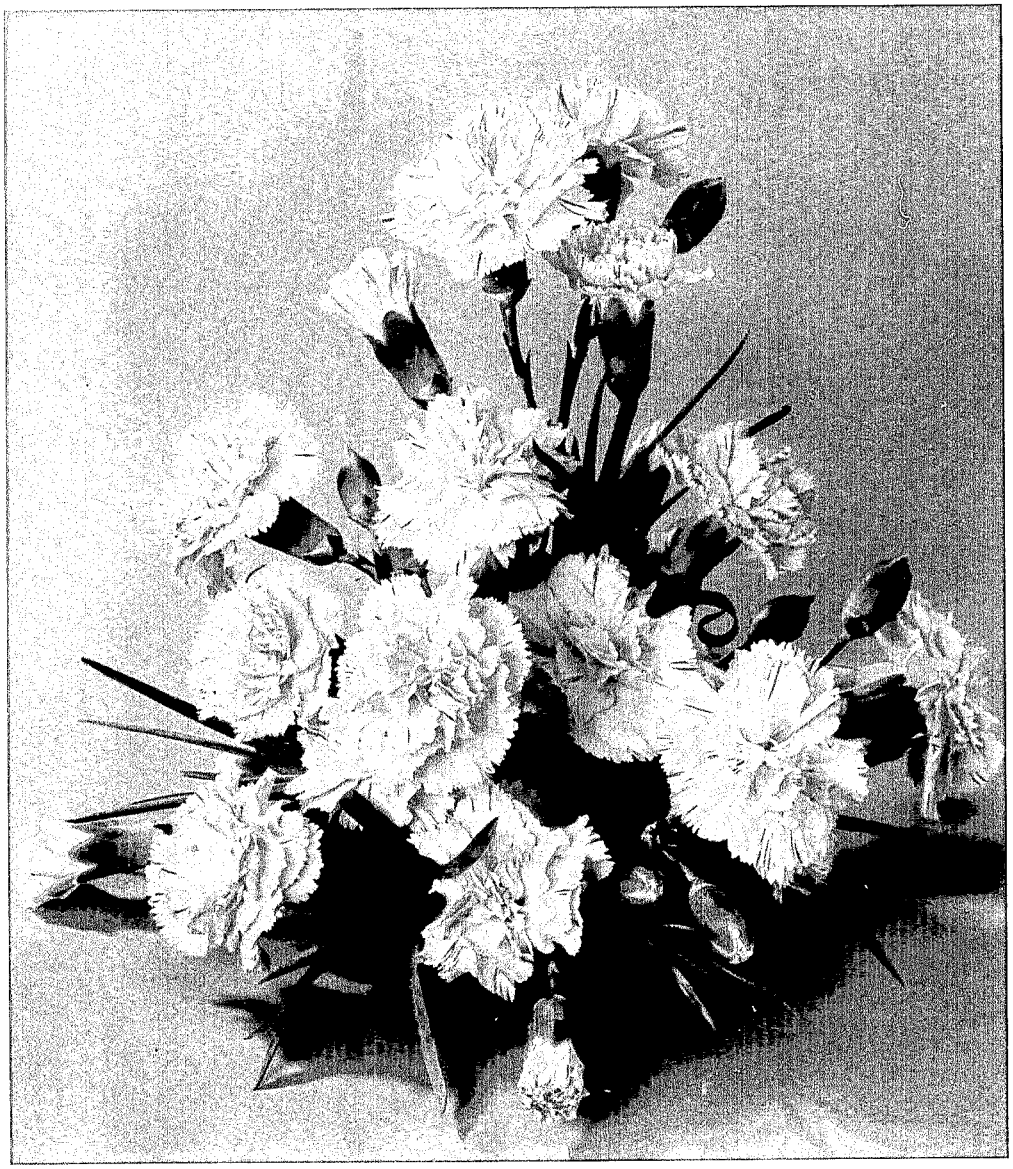

* * * * *